(12) United States Patent
Legay

(10) Patent No.: US 6,230,058 B1
(45) Date of Patent: May 8, 2001

(54) ACTIVE MEDICAL DEVICE HAVING PROTECTED MEMORY REGISTERS FOR STORING ADJUSTABLE PARAMETER VALUES

(75) Inventor: Thierry Legay, Fontenay-les-Briis (FR)

(73) Assignee: Ela Medical S.A., Montrouge (FR)

( * ) Notice: Subject to any disclaimer, the term of this patent is extended or adjusted under 35 U.S.C. 154(b) by 0 days.

(21) Appl. No.: 09/425,032

(22) Filed: Oct. 19, 1999

(30) Foreign Application Priority Data

Oct. 19, 1998 (FR) .................................... 98 13056

(51) Int. Cl.[7] ........................................ A61N 1/08
(52) U.S. Cl. ................................................ 607/59
(58) Field of Search .................. 607/59, 31, 27

(56) References Cited

U.S. PATENT DOCUMENTS

| | | | |
|---|---|---|---|
| 5,031,180 | 7/1991 | McIver et al. .......................... | 371/36 |
| 5,792,201 | 8/1998 | Causey, II et al. ..................... | 607/27 |
| 5,800,473 | 9/1998 | Faissandier ............................ | 607/59 |

FOREIGN PATENT DOCUMENTS

| | | | |
|---|---|---|---|
| 33 12 873 | 10/1984 | (DE) ............................... | G11C/7/00 |
| 3312873 | 10/1984 | (DE) ............................... | G06F/11/16 |
| 0 791 373 | 8/1997 | (EP) ............................... | A61N/1/372 |
| 87 07793 | 12/1997 | (WO) ............................. | H03K/19/23 |

Primary Examiner—Scott M. Getzow
(74) Attorney, Agent, or Firm—Orrick, Herrington & Sutcliffe LLP

(57) ABSTRACT

An active medical device including protected registers for containing digital adjustment parameter values used for the functioning of functional modules of the device. This device includes at least one module (12) for achieving a predetermined device function, this module including a circuit specific for performing the function and which has an adjustable parameter value in the form of a digital word of N bits. Each such module includes a plurality of volatile storage registers having N bits storing the aforementioned digital words, and circuits for comparing (32, 36), the respective contents of the registers and producing an anomaly signal (IT1, IT2 . . . ITi . . . ITk) in the event of a discordance between the contents of the plurality of registers for a given module. The anomaly signal may be an interrupt signal applied to a microcontroller (10). The module also includes a majority circuit (30) receiving at its input the contents of the registers and delivering at its output to the specific circuit (24) the resulting value as the adjustment parameter value to be used in performing the function. It also is contemplated to restore the contents of corrupted registers in the event of a discordance detected by the comparison.

9 Claims, 2 Drawing Sheets

ACTIVE MEDICAL DEVICE HAVING PROTECTED MEMORY REGISTERS FOR STORING ADJUSTABLE PARAMETER VALUES

FIELD OF THE INVENTION

The present invention is directed to "active medical devices" such as those devices defined by the Jun. 20, 1990 directive 93/42/CEE of the Council of the European Communities. Such devices include implantable devices, such as pacemakers, defibrillators and/or cardiovertors, neurological devices, pumps for the diffusion of medical substances, cochlear implants, etc., and nonimplantable devices, such as devices carried by the patient, for example, Holter recorder devices which make it possible to carry out, uninterrupted and over a long period of time, the recording of signals collected by implanted or external electrodes.

BACKGROUND OF THE INVENTION

In active medical devices, as in many other electronic devices, it is necessary to input and store in memory a certain number of operating parameters which are necessary for the device to perform the desired functions.

Among these parameters, one first of all finds parameters of a technical nature, which are generally adjusted at the time of production of the device, or at the time of calibration of the device (e.g., voltage or current references, oscillation frequencies, amplifier gains, etc.). Indeed, the circuit design of the device often requires that the functioning of the hardware circuits be adjusted in order to obtain an optimal behavior. These adjustments can be carried out in various ways, for example, by an adjustment of the resistance by etching, sanding or laser engraving (trimming). More recently, the generalization of electronics with switchable capacitors (capacitors controlled by transistors switches) and digital processing has brought back the problem of adjustment with respect to obtaining a digital code word of N bits which, once obtained, is used via digital-to-analog converters to control the logical switches of a capacitor network, or as a variable in a software routine. Such a technique is, for example, described in the EP-A-0 661 657 and its corresponding U.S. Pat. No. 5,697,960 issued to the assignee hereof, ELA Médical SA.

The value of other technical parameters can be adjusted later on during use. In the particular case of an implantable active medical prosthesis device, certain parameter values can be adjusted by the practitioner after implantation, for example, to adapt the prosthesis to the patient from a physiological point of view. These adjustable parameter values will condition the behavior of the various software control algorithms for the medical device, for example, for the delivery of stimulation pulses or defibrillation shocks in the case of a cardiac prosthesis.

These various parameters have as common characteristics permanent parameters (i.e., these parameters that are adjusted once and for all) or quasi-permanent parameters, and programmable parameters to be defined in the form of digital codes of N bits (N being a number of bits which can vary according to the parameter considered).

These digital codes are thus stored in permanent or nonvolatile memories, which can be ROM with fuses, EPROM, E2PROM, flash memory or battery-backed RAM. Each one of these types of memories has its own advantages and disadvantages, and especially a greater or lesser ability to store the information in a durable or non volatile manner. The RAM, which has the greatest facility of writing data, presents also a greater risk of loss or corruption of information on rare events, such as, for example, the impact of heavy ions such as the alpha particles or the electric parasites likely to be produced, for example, following an exposure to a high intensity electromagnetic pulse.

The ROM, EPROM, E2PROM or flash type of memories are by nature well protected from these risks of deterioration, but they present, for an active medical device, two disadvantages. On the one hand, from the point of view of the topology of the circuits, these memories are not physically located near the circuits where the adjustable parameter value stored in memory is used, and, in addition, are typically organized in a global way on a memory board, which prohibits a direct and permanent access to the stored information, whereas the circuit performing the analog function needs access to this stored information all the time. In the second place, reading data from these memories consumes energy, which is a critical parameter for implantable prostheses, and more generally, for portable battery-powered devices. This constraint prevents a permanent access to the information stored in these memories for calibration of the analog function stored in these memories, for obvious reasons of consumption of energy.

These difficulties can be overcome by storing the information in question (i.e., the parametric values) in registers of the RAM memory or flip-flop logic device type, located inside the circuit module which performs the functions and uses the parameter values. This provides the information stored in circuits topologically near to the place of the function which they calibrate, which circuits are permanently readable with very low current consumption.

These registers, however, are by nature volatile storage registers, and it is necessary to take account of the risk of accidental obliteration or deterioration of the data. This in turn brings about two problems. One is monitoring the information stored in the registers in order to control the integrity of the data, with a negligible power consumption and in an immediate or quasi-immediate manner. Another is correcting, also in an immediate or quasi-immediate manner, the corrupted data in the event of an accidental deterioration.

Various systems have been proposed based on a redundant and/or self-correcting coding of information, for example, of the CRC or analog type. But this technique presents the disadvantages of requiring an examination or analysis of quasi-permanent information, thus implying a large energy consumption, and in addition the appearance of an unspecified state of information during the lapse of time separating the detection of the error from its correction. The latter disadvantage is not acceptable in the case of active medical devices such as pacemakers, in which the continuity of correct functioning must be ensured in all circumstances.

OBJECTS AND SUMMARY OF THE INVENTION

Broadly, the present invention overcomes the aforementioned problems, by proposing an active medical device including at least one module for achieving a function of the device, this module comprising a circuit specific to the function having an adjustable parameter value in the form of a digital word, typically of N bits, such that each such module includes a plurality of registers of the volatile type having the same number of bits, each register storing the aforementioned digital word as the value of the adjustable parameter, and a means for comparing the respective contents of the registers and to produce an anomaly signal in the event of a discordance between the register contents.

Preferably, there are at least three N bit registers in each module, and the module also includes a majority circuit receiving at its input the contents of the registers, and delivering at its output to the specific circuit a digital word which is the adjustment parameter value to be used by the module in performing its function.

When the active medical device is a device with a microcontroller or microprocessor (collectively a "microcontroller"), the anomaly signal can be an interrupt signal applied to the microcontroller interrupt input. In the event that a plurality of modules are employed, the respective interrupt signals can be applied to the microcontroller via a multiplexor, in or together with a related code to manage the priorities as between the different anomaly signal interrupts.

An interrupt signal thus can then be used to process data so as to identify the corrupted data and correct it by copying a correct digital word in the affected register(s). The different modules thus can have different digital words stored as different adjustable parameter values, for performing different functions. Further, the different digital words and the respective plurality of registers associated with a given module can have different numbers of bits from the registers associated with a different module.

Very advantageously, another aspect of the invention provides for restoring the contents of any corrupted register (s) in the event of a discordance detected by the comparison means. The restoring can be obtained by seeking a concordant value between the digital words stored in a plurality of registers, and recopying the concordant value into the corrupted register and circuit means for performing these functions. Alternately, when the value of the adjustable parameter is also preserved in a nonvolatile memory external to the module, the restoring means can function to recopy in the corrupted register, or in all the registers (corrupted and noncorrupted), the value read from the external nonvolatile memory.

BRIEF DESCRIPTION OF THE DRAWINGS

Further characteristic, features and benefits of the invention will become apparent to a person of ordinary skill in the art from the following detailed description, made with reference to the annexed drawings, in which like reference characters refer to like elements, and in which.

DETAILED DESCRIPTION OF THE DRAWINGS

Figure 1:
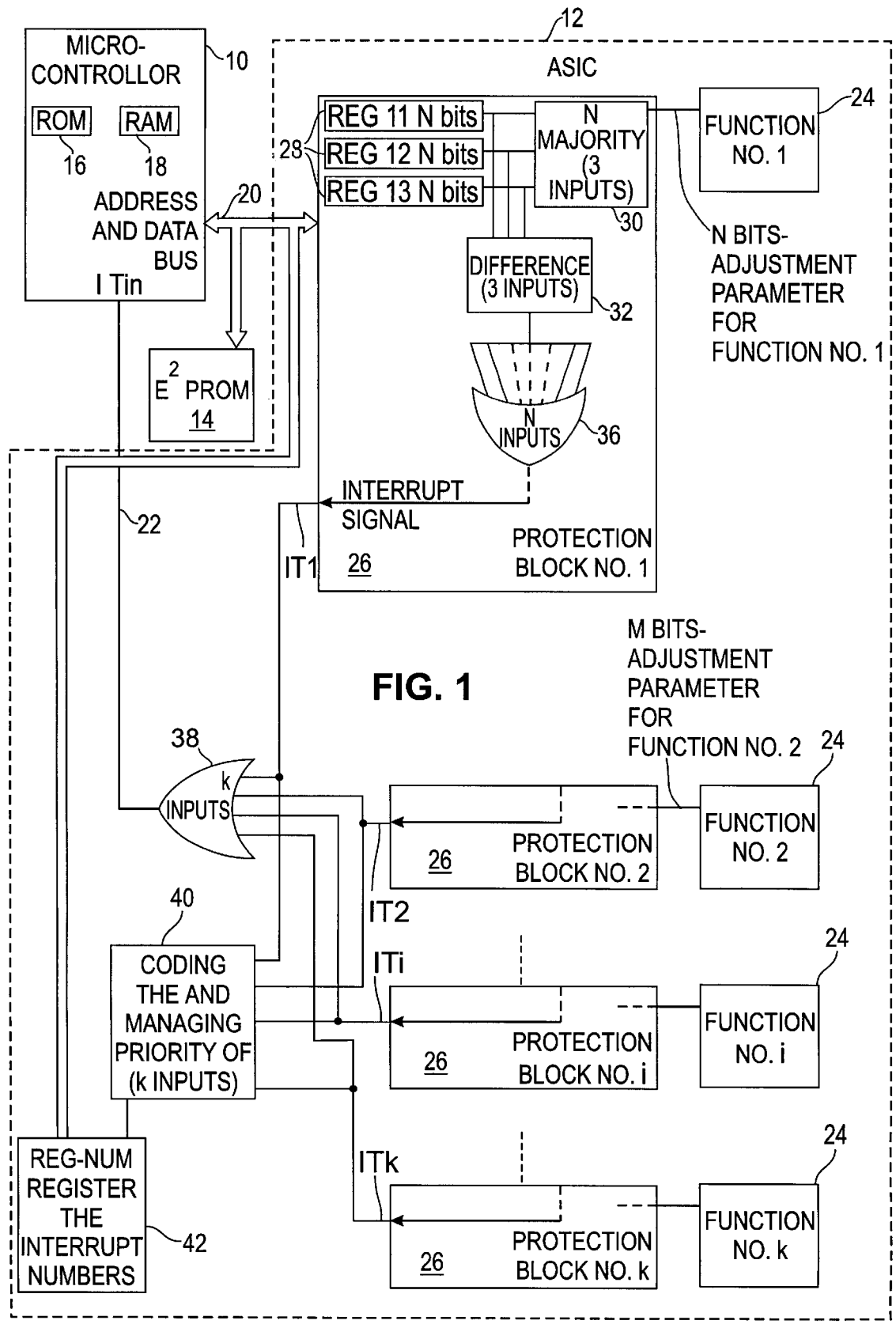
FIG. 1 is a block schematic diagram of the principal elements of an active medical device incorporating the correction and monitoring circuit in accordance with a preferred embodiment of the invention.

The active medical device in which the present invention is employed is composed primarily of a microcontroller 10 and an application specific integrated circuit or ASIC 12 containing the various functions to be configured by adjustable parameter values stored in protected registers.

The device can include a nonvolatile storage memory 14 such as a E2PROM, which can be external, as illustrated, or internal to microcontroller 10.

Microcontroller 10 comprises, in a traditional manner, a read-only memory ROM 16 and a read-write memory RAM 18, and it communicates with the ASIC 12 and, if necessary, the E2PROM 14 via an address and data bus 20. In addition, it has an interrupt input ITin 22, whose role will be explained below.

The ASIC 12 typically comprises a certain number of modules 24 of which each one corresponds to a particular function having an adjustable parameter, the value of which affects the functioning. For example, there are four modules 24 illustrated in FIG. 1 (but more could exist), which could be for (1) amplifying signals with an adjusted gain, (2) an oscillator having an adjusted frequency, (3) a circuit for processing sensed acceleration data, in the case of a rate responsive device (e.g., a pacemaker, a device that senses an acceleration parameter and adjusts the pacing rate as a function of the measured acceleration), and (4) a stimulation circuit with a programmable configuration (that is the configuration of the stimulation electrodes for a multisite pacemaker, or the configuration of the shocks to be applied for a defibrillator).

One also can in the same way store data critical for functioning of the device, for example, the serial number of the model, which is essential data in particular with the recognition of an implanted device by an external programmer.

Each of the various modules 24 (only four modules 24 are shown) are connected to a protection block 26 storing N bits (N being a variable number from one module to the next according to the function considered) necessary to the adjustment of the corresponding module 24.

Figure 2:
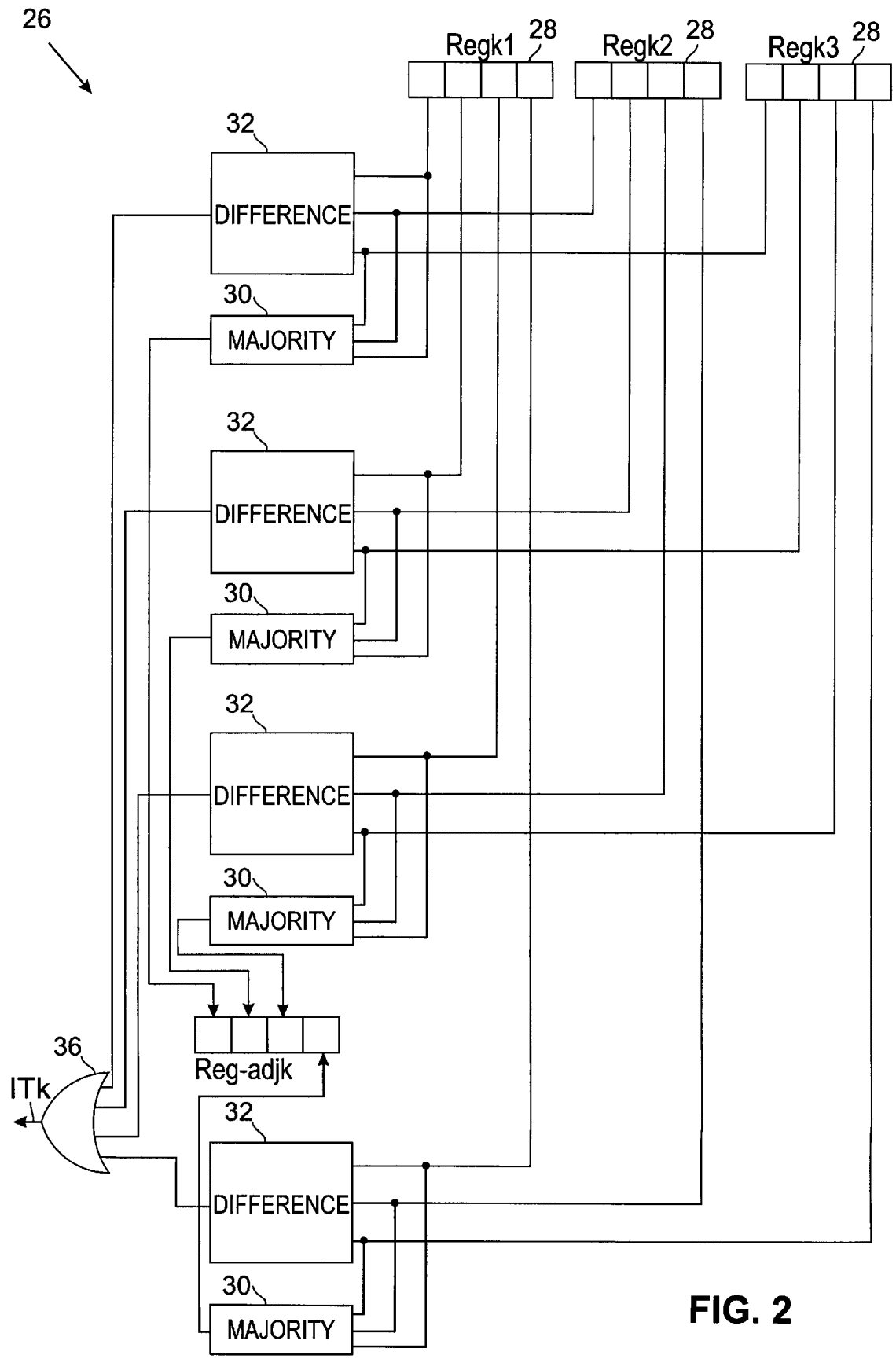
FIG. 2 is a schematic circuit diagram of a protection block of FIG. 1.

The adjustment bits (also referred to as the digital word or the adjustment parameter value), preferably organized in digital words of N bits, are stored in triplicate in identical registers 28, whose architecture is preferably identical from one protection block 26 to the others, but which may differ according to the number N of adjustment bits used for the associated corresponding module 24. FIG. 2 illustrates an example of a protection block 26 where N=4.

It should be understood that the use of three for the number of registers 28 in the illustrated example is not restrictive, and a higher number could be considered, preferably (but not necessarily) an odd number.

Initially, and under the standard operating conditions, the three registers 28 of the same protection block 26 store the same information and number of bits. Each bit of each of three registers 28 of the same protection block 26 is applied, on the one hand, to a corresponding one of the three inputs of a majority circuit 30, and, on the other hand, to a corresponding one of the three inputs of a difference gate 32. The majority circuit 30 uses a truth table having three inputs A, B and C, as follows:

| A | B | C | Majority |
|---|---|---|----------|
| 0 | 0 | 0 | 0 |
| 0 | 0 | 1 | 0 |
| 0 | 1 | 0 | 0 |
| 0 | 1 | 1 | 1 |
| 1 | 0 | 0 | 0 |
| 1 | 0 | 1 | 1 |
| 1 | 1 | 0 | 1 |
| 1 | 1 | 1 | 1 |

The majority circuit 30 outputs are applied to a register Reg_Adj 34 in module 24 (see FIG. 2) allowing for the adjustment of the function of the module 24 associated with the particular protection block 26. Thus, if a deterioration occurs on only one of three registers 28 (or less than a majority in the case that more than three registers 29 are used), no consequence is seen by the adjusted function, which continues to operate with the correct adjustable parameter value.

These majority circuits thus reliably indicate the integrity of the stored data, even if one of the storage registers has suddenly deteriorated or become corrupted, because, in this case the two other registers will remain identical and it is their values which will be taken into account by the majority circuit 30. Consequently, the deterioration which has occurred is not seen by the adjustment function of module 24.

The difference gate 32, by comparing bit by bit the three registers 28, determines that the three registers 28 are always identical (or not). If they are identical (i.e., a normal operating situation), then gates 32 are in an inactive state (power consumption is thus null, although the devices are still always monitoring the input). If a difference appears between the three registers on any of the bits, the function of the corresponding gate 32 goes to an active state, thus revealing the deterioration of data in one of the registers. This provides a discordant result. The truth table for difference gate 32 follows:

| A | B | C | # |
|---|---|---|---|
| 0 | 0 | 0 | 0 |
| 0 | 0 | 1 | 1 |
| 0 | 1 | 0 | 1 |
| 0 | 1 | 1 | 1 |
| 1 | 0 | 0 | 1 |
| 1 | 0 | 1 | 1 |
| 1 | 1 | 0 | 1 |
| 1 | 1 | 1 | 0 |

The circuit will manage the detection of such a deterioration in the following way.

Referring to FIG. 2, the outputs of the difference gates 32 of each protection block 26 are connected to the one of N inputs of a common OR gate 36 (there are as many inputs as there are bits in each register 28 of the given module 24) producing at the output an anomaly signal $IT_K$, making it possible to convey a request for an interrupt to the microcontroller.

Thus, for each function (module 24), only one wire is necessary to convey the interrupt request suitable for the of the corresponding module, regardless of which bit is corrupted in the three registers 28.

The interupted requests $IT_1$, $IT_2$. . . $IT_K$ are gathered and treated by two functions. First, an OR gate 38 with K inputs gathers all the interrupt requests, and its output is interfaced with the interrupt input 22 of microcontroller 10 (FIG. 1). Second, a block 40 with K inputs has as a function to calculate the number of the interrupts which occurred, and to write the number in a register Reg_Num 42, which is visible to the global system by reading register Reg_Num 42 via bus 20. If several interrupts occur at the same time, block 40 stores each request and writes in register 42 the number of the interrupts to be treated, according to preset priorities. The preset priorities establish a relative priorty for correcting the registers of the functional module corrupt when more than one module is corrupted at a given time.

Microcontroller 10, on reception of an interrupt request at input ITin 22, carries out a specific program which can be contained in the ROM 16 or the RAM 18 to deal with the problem of corruption of data in the register which has just occurred. To know which adjustment has just deteriorated, the microcontroller program reads the register Reg_Num 42 to obtain its number, and thus the address of the corrupted register 28.

At least two modes of operation can be envisaged, according to whether the system does or does not have a nonvolatile storage 14 in which are also stored the adjustment parameter values. In the first case, in the absence of a nonvolatile storage unit, i.e., if the adjustable parameter values are exclusively preserved in registers 28, the microcontroller reads the three registers 28 corresponding to the interrupt number indicated by register 42, and checks that at least two of the three registers 28 are identical. If so, the microcontroller then rewrites the third register to be identical with the others registers. If the three registers contain different values, then a concordant value is written into the three registers.

If, on the other hand, the adjustment parameter is stored in a nonvolatile memory 14, then the microcontroller reads the adjustment parameter value corresponding to the interrupt number from this nonvolatile memory and rewrites this value in the three registers 28 concerned (one envisages in this case a maskable interrupt). In the alternative, instead of specifically correcting the registers associated with the register that was deteriorated, all of the registers 28 of all modules can be rewritten with the correct values each time that a deterioration of any register is detected. This manner of proceeding avoids the used of the circuits for coding the interrupts and managing priorities 40 and 42; it is however necessary, in this case, to envisage a maskable interrupt throughout all correction. It will be incidentally noted that, if one stores in nonvolatile memory the adjustment parameter values, the system can manage not only the corruption of the data by parasitic phenomena, but also transitory losses of power.

When the microcontroller has completed the correction process, it restores the monitoring of the system by again authorizing the line of interrupt 22 assigned to the protection of adjustments.

If several interrupt requests had been recorded contemporaneously, after the microcontroller treated the highest priority request, as of the reauthorisation of the protection system, the system again generates an interrupt request with a different coding number in the register Reg_Num 42. The next highest priority interrupt request will then be treated, and so on until all interrupt requests have been treated.

As one of ordinary skill in the art will understand, this correction, managed by a simple interrupt (with priority) of the microprocessor, is very quickly operated, typically in a few milliseconds, which is a very short time, making it possible not to affect the physiological behavior of the active medical device.

One also will note that the integrity of the system is guaranteed even during the phase of correction (which is very short) by the microprocessor of the corrupted data, as a consequence of the majority circuit 30 which continues to apply to the module 24 the correct value, contained in the non-corrupted registers.

One skilled in the art will appreciate that the present invention can be practiced by other than the described embodiment, which are presented for the purposes of illustration and not of limitation.

I claim:

1. An active medical device having a function, including at least one module (12) for achieving said function, said at least one module comprising an adjustable parameter value in the form of a digital word of a plurality of bits and a circuit (24) specific to performing said function in response to said adjustable parameter value, wherein said module further comprises:

at least three registers (28), each register being a volatile type memory storing therein said plurality of bits corresponding to said digital word, means for comparing respectively the digital words stored in the at least three registers, detecting a discordance in the corresponding digital words stored in the at least three registers, and producing an anomaly signal in the event of detected discordance; and a majority circuit (30) having an input receiving the bits stored in the at least three registers and an output coupled to the specific circuit (24), said output being the adjustment parameter value.

2. The device of claim 1, wherein the active medical device further comprises a microcontroller (10) having an interrupt input, and wherein the anomaly signal is an interrupt signal applied to the microcontroller interrupt input.

3. The device of claim 2, further comprising;

a plurality of modules;

a gate having a plurality of inputs coupled respectively to said plurality module anomaly outputs, and an output coupled to the microcontroller interrupt input; and means for coding and managing a priority of each interrupt signal.

4. The device of claim 1, further comprising means, responsive to a detected discordance, for restoring the digital word stored in said at least three registers associated with the detected discordance.

5. The device of claim 4 wherein the restoring means further comprises means for identifying the one of the least three registers associated with the detected discordance as a corrupted register, and means for determining a concordant digital word stored in the at least three registers and recopying said concordant digital word in the corrupted register.

6. The device of claim 4, further comprising a nonvolatile memory external said module, wherein the digital word corresponding to the adjustable parameter is stored in said nonvolatile memory, and wherein the means for restoring further comprises means for recopying in the corrupted register the digital word stored in said external nonvolatile memory.

7. The device of claim 6, wherein the means for recopying recopies said digital word stored in the external nonvolatile memory in each of the at least three registers.

8. The device of claim 1, wherein for at least one of said modules, said digital word further comprises N bits and said means for comparing further comprises means for comparing respective N bits of said digital words.

9. The device of claim 8 wherein for a second of said plurality of modules the digital word comprises M bits, M not equal to N, wherein said second module performs a different function from the first module.

* * * * *

UNITED STATES PATENT AND TRADEMARK OFFICE
CERTIFICATE OF CORRECTION

PATENT NO. : 6,230,058 B1
DATED : May 8, 2001
INVENTOR(S) : Thierry Legay

It is certified that error appears in the above-identified patent and that said Letters Patent is hereby corrected as shown below:

Column 1,
Line 35, delete "transistors switches" and insert -- transistor switches -- therefor;
Line 56, delete "these parameters" and insert -- those parameters -- therefor;

Column 3,
Line 11, delete "are employed" and insert -- is employed -- therefor;
Line 41, delete "characteristic" and insert -- characteristics -- therefor;

Column 5,
Line 34, delete "to the one" and insert -- to one -- therefor;
Line 41, delete "the of" and insert -- the adjustment of -- therefor;
Line 44, delete "interrupted requests" and insert -- interrupt requests -- therefor;
Line 55, delete "relative priorty" and insert -- relative priority -- therefor;
Line 56, delete "module corrupt" and insert -- module corrupted -- therefor;

Column 6,
Line 21, delete "the used" and insert -- the use -- therefor;
Line 24, delete "all correction" and insert -- all corrections -- therefor;
Line 55, delete "embodiment" and insert -- embodiments -- therefor;
Line 67, delete "word," and insert -- word; -- therefor;

Column 7,
Line 14, delete "comprising;" and insert -- comprising: -- therefor; and
Line 27, delete "the least" and insert -- the at least -- therefor;

Signed and Sealed this

Twenty-eighth Day of June, 2005

JON W. DUDAS
*Director of the United States Patent and Trademark Office*